(12) United States Patent
Liker

(10) Patent No.: US 9,017,742 B2
(45) Date of Patent: *Apr. 28, 2015

(54) USING POMEGRANATE EXTRACTS FOR INCREASING PROSTATE SPECIFIC ANTIGEN DOUBLING TIME

(71) Applicant: POM Wonderful, LLC, Los Angeles, CA (US)

(72) Inventor: Harley Liker, Los Angeles, CA (US)

(73) Assignee: POM Wonderful, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/067,754

(22) Filed: Oct. 30, 2013

(65) Prior Publication Data

US 2014/0056930 A1    Feb. 27, 2014

Related U.S. Application Data

(63) Continuation of application No. 13/466,849, filed on May 8, 2012, now Pat. No. 8,597,699, which is a continuation of application No. 12/282,800, filed as application No. PCT/US2007/064112 on Mar. 15, 2007, now Pat. No. 8,178,137.

(60) Provisional application No. 60/782,437, filed on Mar. 15, 2006.

(51) Int. Cl.
*A61K 36/185* (2006.01)
*A61K 39/00* (2006.01)

(52) U.S. Cl.
CPC ............... *A61K 39/00* (2013.01); *A61K 36/185* (2013.01)

(58) Field of Classification Search
USPC .................................................. 424/777, 725
IPC ....................................................... A61K 36/18
See application file for complete search history.

(56) References Cited

U.S. PATENT DOCUMENTS

| | | | |
|---|---|---|---|
| 5,840,308 A | 11/1998 | Jassim et al. | |
| 5,902,616 A * | 5/1999 | Hinnergardt et al. | ........... 426/52 |
| 6,033,692 A | 3/2000 | Chukwu | |
| 6,060,063 A | 5/2000 | Lansky et al. | |
| 6,312,753 B1 | 11/2001 | Kealey et al. | |
| 6,361,807 B1 | 3/2002 | Aviram et al. | |
| 6,375,993 B1 | 4/2002 | Aviram et al. | |
| 6,387,370 B1 | 5/2002 | Yegorova | |
| 6,387,418 B1 | 5/2002 | Aviram et al. | |
| 6,544,581 B1 | 4/2003 | Shrikhande et al. | |
| 6,641,850 B1 | 11/2003 | Aviram et al. | |
| 6,642,277 B1 | 11/2003 | Howard et al. | |
| 6,800,292 B1 | 10/2004 | Murad | |
| 6,855,352 B2 | 2/2005 | Shoji | |
| 6,977,089 B1 * | 12/2005 | Aviram et al. | ................. 424/769 |
| 7,611,738 B2 * | 11/2009 | Bates et al. | .................... 424/769 |
| 7,632,527 B2 * | 12/2009 | Jochim et al. | .................. 424/725 |
| 7,645,469 B2 * | 1/2010 | Aviram et al. | ................. 424/777 |
| 7,727,563 B2 * | 6/2010 | Aviram | ......................... 424/777 |
| 7,780,998 B2 * | 8/2010 | Aviram et al. | ................. 424/777 |
| 8,178,137 B2 * | 5/2012 | Liker | ............................ 424/769 |
| 8,334,000 B2 * | 12/2012 | Greenway et al. | ............. 424/725 |
| 8,597,699 B2 * | 12/2013 | Liker | ............................ 424/769 |
| 2002/0012710 A1 * | 1/2002 | Lansky | ......................... 424/725 |
| 2002/0197341 A1 * | 12/2002 | Lansky | ......................... 424/769 |
| 2003/0134006 A1 | 7/2003 | Chukwu | |
| 2004/0009262 A1 | 1/2004 | Chukwu | |
| 2004/0126470 A1 | 7/2004 | Harpaz | |
| 2005/0118312 A1 * | 6/2005 | Lansky | ....................... 426/330.3 |

FOREIGN PATENT DOCUMENTS

| | | | |
|---|---|---|---|
| JP | 11243911 A | * | 9/1999 |
| JP | 2003102431 A | * | 4/2003 |
| WO | 00/56177 | | 9/2000 |
| WO | 2006/127832 | | 11/2006 |

OTHER PUBLICATIONS

Seeram et al. "Bioavailability of ellagic acid in human plasma after consumption of ellagitannins from pomegranate (*Punica granatum* L.) juice", Clinica Chimica Acta 348 (2004) 63-68.

Seeram, et al., "Pomegranate Juice Ellagitannin Metabolites Are Present in Human Plasma and Some Persist in Urine for Up to 48 Hours", Journal of Nutrition, 2006, 2481-2485.

Seeram, et al. "Pomegranate Juice and Extracts Provide Similar Levels of Plasma and Urinary Ellagitannin Metabolites in Human Subjects" Journal of Medicinal Food, 11 (2) 2008, 390-394.

(Continued)

*Primary Examiner* — Chris R Tate

(74) *Attorney, Agent, or Firm* — Cotman IP Law Group, PLC

(57) ABSTRACT

A method of increasing a prostate specific antigen (PSA) doubling time in treating a patient. A subject with rising serum PSA is selected. A composition is administered to the subject comprising a therapeutically effective amount of a pomegranate extract comprising a higher content of high molecular weight polyphenol compared to pomegranate juice from arils. The therapeutically effective amount increases a prostate specific antigen doubling time. The pomegranate extract is formed from an insoluble byproduct component obtained by placing pomegranate solids in an aqueous solution, heating the aqueous solution to between about 60° F. to about 210° F., adding at least one enzyme to the aqueous solution, and removing residual insoluble solid materials from the aqueous solution.

18 Claims, 3 Drawing Sheets

(56) References Cited

OTHER PUBLICATIONS

D. Syed, et al. "Photochemopreventive Effect of Pomegranate Fruit Extract on UVA-mediated Activation of Cellular Pathways in Normal Human Epidermal Keratinocytes" Photochemistry and Photobiology, 2006, 82: 398-405.

Adams, et al. "Pomegranate Juice, Total Pomegranate Ellagitannins, and Punicalagin Suppress Inflammatory Cell Signaling in Colon Cancer Cells" Journal of Agricultural and Food Chemistry, 2006, 54, 980-985.

V. Adhami, et al. "Polyphenols from green tea and pomegranate for prevention of prostate cancer" Free Radical Research, Oct. 2006; 40(10): 1095-1104.

S. Kasimsetty, et al. "Effects of Pomegranate Chemical Constituents/ Intestinal Microbial Metabolites on CYP1 B1 in 22Rv1 Prostate Cancer Cells" Journal of Agriculture and Food Chemistry, 2009, 57, 10636-10644.

Sartippour, et al., "Ellagitannin-rich pomegranate extract inhibits angiogenesis in prostate cancer in vitro and in vivo" International Journal of Oncology, 2008, 32:475-480.

Rettig, et al. "Pomegranate extract inhibits androgen-independent prostate cancer growth through a nuclear factor-KB-dependent mechanism" Molecular Cancer Therapy, 2008; 7(9): 2662-71.

Seeram, et al. "Pomegranate Ellagitannin-Derived Metabolites Inhibit Prostate Cancer Growth and Localize to the Mouse Prostate Gland" Journal of Agricultural and Food Chemistry, 2007, 55, 7732-7737.

Hong, et al. "Pomegranate polyphenols down-regulate expression of androgensynthesizing genes in human prostate cancer cells overexpressing the androgen receptor" Journal of Nutritional Biochemistry, 2008, 8 pages.

J. Trombold, et al. "Ellagitannin Consumption Improves Strength Recovery 2-3 d after Eccentric Exercise" The American College of Sports Medicine, 2010, 493-498.

B. Fuhrman, et al. "Pomegranate juice polyphenols increase recombinant paraoxonase-1 binding to high-density lipoprotein: Studies in vitro and in diabetic patients" Nutrition 26 (2010) 359-366.

J. Khateeb, et al. "Paraoxonase 1 (PON1) expression in hepatocytes is upregulated by pomegranate polyphenols: A role for PPAR" Atherosclerosis, 2009, 7 pages.

M. Davidson, et al. "Effects of Consumption of Pomegranate Juice on Carotid Intima-Media Thickness in Men and Women at Moderate Risk for Coronary Heart Disease" American Journal of Cardiology, 2009, 936-942.

O. Rozenberg, et al. Pomegranate juice sugar fraction reduces macrophage oxidative state, whereas white grape juice sugar fraction increases it Atherosclerosis, 188 (2006) 68-76.

Mattiello, et al. "Effects of Pomegranate Juice and Extract Polyphenols on Platelet Function" Journal of Medicinal Food, 12 (2) 2009, 7 pages.

Sumner, et al. "Effects of Pomegranate Juice Consumption on Myocardial Perfusion in Patients With Coronary Heart Disease" American Journal of Cardiology, 2005, 5 pages.

M. Aviram, et al. "Pomegranate juice consumption inhibits serum angiotensin converting enzyme activity and reduces systolic blood pressure" Atherosclerosis, 158 (2001) 195-198.

M. Aviram, et al. "Pomegranate Phenolics from the Peels, Arils, and Flowers Are Antiatherogenic: Studies in Vivo in Atherosclerotic Apolipoprotein E-Deficient (EO) Mice and in Vitro in Cultured Macrophages and Lipoproteins" Journal of Agricultural and Food Chemistry, 2008, 56, 1148-1157.

Shiner et al. "Macrophage paraoxonase 2 (PON2) expression is up-regulated by pomegranate juice phenolic anti-oxidants via PPAR and AP-1 pathway activation" Atherosclerosis, 2007, 9 pages.

de Nigris, et al. "Effects of a Pomegranate Fruit Extract rich in punicalagin on oxidation-sensitive genes and eNOS activity at sites of perturbed shear stress and atherogenesis" Cardiovascular Research, 2007, 73, 414-423.

de Nigris, et al. "Pomegranate juice reduces oxidized low-density lipoprotein downregulation of endothelial nitric oxide synthase in human coronary endothelial cells" Nitric oxide, 2006 15259-263.

L. Ignarro, et al. "Pomegranate juice protects nitric oxide against oxidative destruction and enhances the biological actions of nitric oxide" Nitric oxide, 2006,15,93-102.

de Nigris et al. "Beneficial effects of pomegranate juice on oxidation-sensitive genes and endothelial nitric oxide synthase activity at sites of perturbed shear stress" Proceedings of the National Academy of Sciences, 2005, vol. 102, No. 13,6 pages.

Rosenblat, et al. "Pomegranate Byproduct Administration to Apolipoprotein EDeficient Mice Attenuates Atherosclerosis Development as a Result of Decreased Macrophage Oxidative Stress and Reduced Cellular Uptake of Oxidized Low-Density Lipoprotein" Journal of Agricultural and Food Chemistry, 2006,54, 1928-1935.

de Nigris, et al. "The influence of pomegranate fruit extract in comparison to regular pomegranate juice and seed oil on nitric oxide and arterial function in obese Zucker rats" Nitric Oxide, 2007 17, 50-54.

Kaplan, et al. "Pomegranate Juice Supplementation to Atherosclerotic Mice Reduces Macrophage Lipid Peroxidation, Cellular Cholesterol Accumulation and Development of Atherosclerosis" Journal of Nutrition, 2001, 2082-2089.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007, 83: 882-888.

Lorean et al. "Maternal Dietary Supplementation with Pomegranate Juice Is Neuroprotective in an Animal Model of Neonatal Hypoxic-Ischemic Brain Injury" Pediatric Research, 2005, vol. 57, No. 6, 7 pages.

Shah, et al. "Pomegranate juice decreases amyloid load and improves behavior in a mouse model of Alzheimer's disease" Neurobiology of Disease, 2006, Abstract.

D. Bialonska, et al. "Urolithins, Intestinal Microbial Metabolites of Pomegranate Ellagitannins, Exhibit Potent Antioxidant Activity in a Cell-Based Assay" Journal of Agriculture and Food Chemistry, 2009, 57, 10181-10186.

Y. Zhang, et al. "Absence of Pomegranate Ellagitannins in the Majority of Commercial Pomegranate Extracts: Implications for Standardization and Quality Control" Journal of Agricultural and Food Chemistry, 2009,57,7395-7400.

Y. Zhang, et al. "International Multidimensional Authenticity Specification (IMAS) Algorithm for Detection of Commercial Pomegranate Juice Adulteration", Journal of Agricultural and Food Chemistry, 2009, 9 pages.

S. Madrigal-Carballo, et al. "Pomegranate (*Punica granatum*) supplements: authenticity, antioxidant and polyphenol composition" Journal of Functional Foods, 2009, 6 pages.

K. Martin et al. "Development of a novel pomegranate standard and new method for the quantitative measurement of pomegranate polyphenols" Journal of Science of Food and Agriculture, 2009; 89:157-162.

N. Seeram, et al. "Comparison of Antioxidant Potency of Commonly Consumed Polyphenol-Rich Beverages in the United States" Journal of Agricultural and Food Chemistry, 2008, 56,1415-1422.

Rosenblat, et al. "Consumption of polyphenolic-rich beverages (mostly pomegranate and black currant juices) by healthy subjects for a short term increased serum antioxidant status, and the serum's ability to attenuate macrophage cholesterol accumulation" Food & Function, 2010, 1, 99-109.

G. Borges, et al. "Comparison of the polyphenolic composition and antioxidant activity of European commercial fruit juices" Food & Function, 2010, 11 pages.

A. Sundararajana, et al. "Influenza virus variation in susceptibility to inactivation by pomegranate polyphenols is determined by envelope glycoproteins" Elsevier, 2010 (1-9).

R. Oliveira, et al. "Effects of feeding polyphenols from pomegranate extract on health, growth, nutrient digestion, and immunocompetence of calves" American Dairy Science Association, 2010, 93:4280-4291.

M. Haidari, et al. "Pomegranate(Punicagranatum) purified polyphenol extract inhibits influenza virus and has a synergistic effect with oseltamivir" Phytomedicine, 2009, 10 pages.

(56) References Cited

OTHER PUBLICATIONS

D. Bialonska, et al. "The influence of pomegranate by-product and punicalagins on selected groups of human intestinal microbiota" International Journal of Food Microbiology, 140 (2010) 175-182.

M. Reddy, et al. "Antioxidant, Antimalarial and Antimicrobial Activities of Tannin-Rich Fractions, Ellagitannins and Phenolic Acids from *Punica granatum* L." Planta Medica, 2007, 7 pages.

M. Shukla, et al. "Consumption of hydrolyzable tannins-rich pomegranate extract suppresses inflammation and joint damage in rheumatoid arthritis" Nutrition, 24, 2008,733-743.

Z. Rasheed, et al. "Polyphenol-rich pomegranate fruit extract (POMx) suppresses PMACI-induced expression of pro-inflammatory cytokines by inhibiting the activation of MAP Kinases and NF-KB in human KU812 cells" Journal of Inflammation, 2009, 12 pgs.

Glycaemic Index Research Service "A Study to Measure the Glycaemic Index Value of Pomegranate Juice" The School of Molecular and Microbial Biosciences at Sydney University, Mar. 2009, 22 pgs.

B. McFarlin, et al. "Pomegranate seed oil consumption during a period of high-fat feeding reduces weight gain and reduces type 2 diabetes risk in CD-1 mice" British Journal of Nutrition, 2008, 6 pages.

W. Rock, et al. "Consumption of Wonderful Variety Pomegranate Juice and Extract by Diabetic Patients Increases Paraoxonase 1 Association with High-Density Lipoprotein and Stimulates Its Catalytic Activities" Journal of Agricultural and Food Chemistry, 2008, 56, 8704-8713.

M. Rosenblat, et al. "Anti-oxidative effects of pomegranate juice (PJ) consumption by diabetic patients on serum and on macrophages" Atherosclerosis, 187 (2006) 363-371.

Q. Zhang, et al. "Dietary antioxidants improve arteriogenic erectile dysfunction" International Journal of Andrology, 33, 2010, 1-11.

K. Azadzoi, et al."Oxidative Stress in Arteriogenic Erectile Dysfunction: Prophylactic Role of Antioxidants" Journal of Urology, 2005, vol. 174, 386-393.

Forest, et al. "Efficacy and safety of pomegranate juice on improvement of erectile dysfunction in male patients with mild to moderate erectile dysfunction: a randomized, placebo-controlled, double-blind, crossover study" International Journal of Impotence Research, 2007, 1-4.

S. Strum, et al. "Pomegranates and Prostate Health: A Research Report", PCRI Insights, 2008, vol. 11: No. 3, 36 pages.

A. McCutcheon, et al. "Scientific and Clinical Monograph for POM Wonderful Pomegranate Juice" American Botanical Council, 2008, 20 pgs.

M. Aviram, et al. "Pomegranate juice flavonoids inhibit low-density lipoprotein oxidation and cardiovascular diseases: Studies in atherosclerotic mice and in humans" Drugs Under Experimental and Clinical Research XXVIII, 2003, 15 pages.

M. Warren, et al. "Pomegranate's Ancient Roots to Modern Medicine, Pomegranates: Ancient Roots to Modern Medicine" Taylor and Francis, 2006, 158-166.

D. Heber, et al. "Safety and Antioxidant Activity of a Pomegranate Ellagitannin-Enriched Polyphenol Dietary Supplement in Overweight Individuals with Increased Waist Size" Journal of Agricultural and Food Chemistry, 2007, 55, 10050-10054.

D. Farkas, et al. "Pomegranate Juice Does Not Impair Clearance of Oral or Intravenous Midazolam, a Probe for Cytochrome P450-3A Activity: Comparison With Grapefruit Juice" Journal of Clinical Pharmacology, 2007; 47;286-294.

F. Afaq, et al. "Protective effect of pomegranate-derived products on UVBmediated damage in human reconstituted skin" Experimental Dermatology, 2009.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007.

D Perez et al., Wine, Diet, Antioxidant Defenses and Oxidative Damage. Annals of the New York Academy of Sciences (2002),957:136-145.

KJ Joshipura, et al., The Effect of Fruit and Vegetable Intake on Risk for Coronary Heart Disease. Annals of Internal Medicine (2001),134: 11 06-1114.

http://www.wonderfulpomegranateresearch.com/featured.

Rosenblat et al. "Pomegranate Juice Protects Macrophages from Triglyceride Accumulation: Inhibitory Effect on DGAT1 Activity and on Triglyceride Biosynthesis" Ann Nutr Metab 2011 ;58: 1-9.

Malik Arshi et al "Pomegrante fruit juice for chemoprevention and chemotherapy of prostate cancer," Proceedings of the National Academy of Sciences of USA, vol. '102, No. 41, Oct. 11, 2005: pp. 14813-1418.

Aviram et aL "Pomegranate ,juice consumption reduces oxidative stress; atherogenic modifications to LDI, and platelet aggregation Studies in humans and in atherosclerotic epolipoprotein E-deficient mice;" American Journal of Clinical Nutrition 200005 US, vol. 7'1, No. 5, May 2000, pp. 1062-1076.

Malik Arshi et al "Prostate cancer prevention through pomegranate fruit," Cell Cycle, Feb. 2005, '/01. 5; No. 4 Feb. 2006, pp. 371-373.

Pantuck A. J. et al "83'1. Phase II study of pomegranate juice for men With rising PSA following surgery or radiation for prostate cancer," Journal of Urology, Lippincott Wiliiams & Wilkins, Baltimore MD. US, vol. 17, No. 4. Suppl S, Apr. 1, 2005, pp. 225-226.

Kim Nam Deuk et al. "Chemopreventive and adjuvant therapeutic potential of pomegranate (*Punica granatum*) for human breast cancer," Breast Cancer Research and Treatment; vol. 71, No. 3, Feb. 2002, pp. 203-217.

Pantuck A J. el al "Phase II study of pomegranate juice for men with rising prostrate-specific antigen following surgery; or radiation for prostate cancer," Clinical Cancer Research 20060701, vol. '12, No. '13, Jul. 1, 2006, pp. 4018-4026.

Supplementary European Search Report for EP Application No. EP 07 75 8647, mailed on Jan. 29, 2010. 9 Pages.

Pantuck, et al., "Pomegranate Juice May Slow Prostate Cancer Growth," American Urological Association Annual Meeting, The Journal of Urology (Texas, US), vol. 173 (No. 4), pp. 1 057-1439 (May 24, 2005).

Albrecht, et al., "Pomegranate Extracts Potently Suppress Proliferation, Xenograft Growth, and Invasion of Human Prostate Cancer Cells," European Urology Supplements, vol. 2, Issue 6,24-27 p. 138 (Sep. 2003).

Seeram, et al., "In vitro antiproliferative, apoptotic and antioxidant activities of punicalagin, ellagic acid and a total pomegranate tannin extract are enhanced in combination with other polyphenols as found in pomegranate juice," D Journal of Nutritional Biochemistry, 16(6) pp. 360-367 (2005).

International Search Report, dated Oct. 17, 2007.

International Preliminary Report on Patentability, dated Sep. 16, 2008.

* cited by examiner

USING POMEGRANATE EXTRACTS FOR INCREASING PROSTATE SPECIFIC ANTIGEN DOUBLING TIME

This application is a continuation of U.S. patent application Ser. No. 13/466,849 filed on May 8, 2012, which is a continuation of U.S. patent application Ser. No. 12/282,800, filed on Sep. 12, 2008, which is the National Stage of International Application No. PCT/US07/64112, filed Mar. 15, 2007, which claims benefit of U.S. Provisional Patent Application Ser. No. 60/782,437, filed Mar. 15, 2006, the specifications of which are hereby incorporated by reference.

BACKGROUND OF THE INVENTION

1. Field of the Invention

The present invention relates generally to pomegranate extracts and methods of using thereof for treating prostate cancer in a way that increases prostate specific antigen doubling time.

2. Description of the Related Art

Phytochemicals in edible plants can have cancer preventative benefits through antioxidation and via gene-nutrient interactions. Pomegranate juice has been shown to be a rich source of polyphenolic flavonoids. Pomegranate juice possesses impressive antioxidative properties due to its high flavonoids content, mainly the water soluble tannins and proanthocyanins.

Prostate cancer is the most common invasive malignancy and the second leading cause of cancer-related deaths among U.S. males, with a similar trend in many Western countries. Biological aggressiveness of prostate cancer is directly related to tumor volume, and tumor volume is proportional to serum prostate specific antigen (PSA). Age is the most common risk factor, with nearly 70 percent of prostate cancer cases occurring in men age 65 and older. The higher a man's PSA level, the more likely it is that cancer is present. However, recent research found prostate cancer in men with PSA levels below 4.0 ng/ml. Most men with an elevated PSA test turn out not to have cancer; only 25 to 30 percent of men who have a biopsy due to elevated PSA levels actually have prostate cancer. A prostate biopsy is the main method used to further diagnose prostate cancer.

Many patients who undergo surgery or radiation therapy to treat localized prostate cancer experience an increase in PSA level after treatment. One of methods being used is measurement of PSA velocity, which is based on changes in PSA levels over time. A sharp rise in the PSA level raises the suspicion of cancer. The rate at which the PSA level is rising for patient, after radical prostatectomy or radiation therapy for localized prostate cancer, is known to correlate with aggressiveness and growth rate of the cancer thus a rapidly rising PSA is correlated with worse patient outcomes and vice-versa. In a study of untreated patients with prostatic carcinomas, patients with shorter doubling times were found with higher clinical stages and worse histological grades whereas patients with longer doubling time were found to have more favorable outcome with low grade tumors on deferred treatment. In men with prostate cancer that has been treated with combined hormone and radiation therapy, a post treatment PSA doubling time of < or =8 months is associated with worse clinical outcomes and may be an early surrogate marker for decreased survival.

Various studies described in vitro cancer chemopreventive properties, including anti-proliferative and pro-apoptotic effects, of different pomegranate compositions on various cancer cell lines. Several studies investigated effects of pomegranate compositions on prostate cancer cell lines. The Lansky et al. studies observed different pomegranate mixture on inhibition of human prostatic adenocarcinoma PC-3 invasion and proliferation across Matrigel and inhibition of phospholipase A-2 expression associated with invasive potential. The Malik et al. study described pomegranate fruit extract on inhibition of cell growth followed by apoptosis of PC-3 through modulations in the cyclin kinase inhibitor-cyclin-cyclin dependent kinase (cdk) signal transduction pathways. The Malik et al. study also described pomegranate fruit extract administration to athymic nude mice implanted with androgen-sensitive human prostatic CWR22Rv1 cells resulted in a significant inhibition in tumor growth concomitant with a significant decrease in serum prostate-specific antigen levels. The results of pomegranate in vitro antitumor activity on human prostatic cancer cell lines and in vivo xenograft of CWR22Rv1 cell only suggest possible cancer-chemopreventive as well as cancer-chemotherapeutic effects for in vivo treatment of prostate cancer in human.

The Albrecht et al. study observed in vitro antitumor activities of pomegranate extracts on cell proliferation, cell cycle distribution, apoptosis, gene regulation, and tumor growth for PC-3, human prostatic carcinoma LNCaP, and human prostatic carcinoma DU145 human cancer cell lines whereas normal prostate epithelial cells (hPrEC) were significantly less negatively affected. The Albrecht et al. study also observed potent inhibition on tumor growth for in vivo xenograft of PC-3 in athymic nude mice injected subcutaneously with pomegranate extracts. The observation of subcutaneous injection of pomegranate extract on the growth inhibition of in vivo xenograft of PC-3 in nude mice does not validate in vivo treatment of prostate cancer in human subjects because it is not known if any administration of pomegranate extract have an antitumor activity on prostate cancer in human.

In vitro tests and in vivo animal tests are necessary to evaluate potential therapeutic effect of pomegranate compositions prior to clinical evaluations. The translation of in vitro and in vivo studies from the laboratory into the clinical trial in human is necessary to obtain and validate anticancer therapeutics for efficacy and toleration as numerous human trials of anticancer drugs have not advanced to a definitive assessment of clinical efficacy in a clinical trial. Prior to the present invention, none of prior art studies have advanced pomegranate juice to a phase II trial for treating prostate cancer. The purpose of a phase II trial of a new anticancer drug is to determine whether the drug has sufficient activity against a specified type of tumor to warrant its further development.

BRIEF SUMMARY OF THE INVENTION

The present invention is based on the discovery that pomegranate juice consumption by a patient may be used to treat prostate cancer. Prior to the present invention, it has been observed that various pomegranate compositions have cancer chemopreventive properties on various in vitro treatment of human prostate cancer cell lines and in vivo treatment of human prostate cancer cell lines xenografted in athymic nude mice. Until the discovery of the present invention, it was not known if there is an efficacy for treating prostate cancer in human patient by any route of administration.

The present invention provides a method of treating a subject with prostate cancer a composition comprising a therapeutically effective amount of an extract from pomegranate fruit. The extract of pomegranate may be a juice extract of pomegranate, an extract from inner or outer peel of pomegranate, or mixture thereof.

According to an embodiment of the present invention, pomegranate juice may be used to treat subjects with rising serum PSA after prostate surgery or radiotherapy. The present invention describes efficacy of pomegranate juice treatment, which shows in vivo effect on increasing PSA doubling time for subjects with prostate cancer post-surgery or radiation with rising PSA level. The cancer chemotherapeutic properties of pomegranate juice is further evidenced by another embodiment of the present invention which provides for a method in that serum derived from subjects on daily pomegranate juice administration for in vitro treatment of human prostate cancer cell line which show anti-proliferative and pro-apoptotic actions. Other objects, features and advantages of the present invention will become apparent to those skilled in the art from the detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications and equivalents thereof.

DETAILED DESCRIPTION OF THE INVENTION

Figure 1:
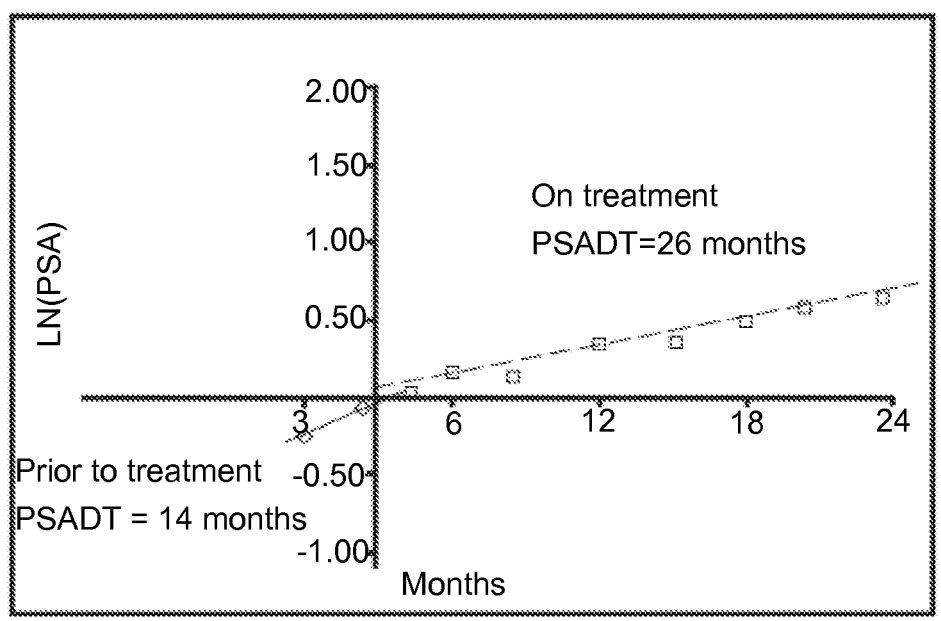
FIG. 1 shows LN(PSA) plotted over time in 1 patient before and during pomegranate juice treatment demonstrating a statistically and clinically significant prolongation of the PSADT with pomegranate juice treatment.

One aspect of the present invention provides a method for treating a patient with prostate cancer. The method comprises the step of administering to the patient a composition comprising a therapeutically effective amount of an extract from pomegranate.

For the purpose of the present invention, an extract from pomegranate may be an extract from the whole pomegranate fruit or from any constituents of pomegranate fruit. Examples of constituents of pomegranate fruit that may be used to make the extract of the present invention include, but are not limited to, juice, seed, and the inner and outer peel of pomegranate fruit. In one embodiment of the present invention, the extract is the juice extract of whole pomegranate fruit. In another embodiment of the present invention, the extract is from the inner or outer peel of pomegranate fruit. In a further embodiment of the present invention, the extract may be a mixture of two or more extracts of the whole pomegranate or any constituents of pomegranate. The term "phytochemicals" generally refers collectively to compounds which are naturally-occurring in the pomegranate and to reaction products and metabolites of these compounds, which are considered to have a beneficial effect on the human health. Examples of such phytochemicals include, but are not limited to polyphenols, estrogens and phytoestrogens. The term "polyphenols" refers generally to a family of naturally-occurring compounds in the pomegranate and includes phenols and polyphenols. Phenols are a class of chemical compounds consisting of a single phenol unit in their structure. Although similar to alcohols, phenols have unique properties including relatively higher acidities due to the aromatic ring tightly coupled to the oxygen and a relatively loose bond between the oxygen and the hydrogen. Examples of phenolic compounds within this group include ellagic acid and gallic acid. Polyphenols are a group of compounds, characterized by the presence of more than one phenolic group. Polyphenols include tannins (e.g., ellagitannins and gallotannins), flavonoids (e.g., anthocyanins and isoflavones) and stilbenes (e.g., resveratrol). The term "pomegranate juice" refers to the juice that is substantially obtained from the arils of the pomegranate. The term "pomegranate solids" refers to any one or a combination of the pericarp, the inner membrane and seeds of a pomegranate.

Methods of making the extract, including the juice from whole pomegranate fruits are described in U.S. Pat. No. 6,977,089 entitled "METHODS OF USING POMEGRANATE EXTRACTS FOR CAUSING REGRESSION IN LESIONS DUE TO ARTERIOSCLEROSIS" and in U.S. patent application Ser. No. 11/137,248 entitled "PROCESSES FOR EXTRACTING PHYTOCHEMICALS FROM POMEGRANATE SOLIDS AND COMPOSITIONS AND METHODS OF USE THEREOF" both of which are incorporated herein by reference. In general, any methods that may produce pomegranate extract and juice that naturally occurs in pomegranate may be used. For the purpose of the present invention, the juice may be concentrated or diluted from its natural concentration. The juice may also be mixed with extracts of other constituents of pomegranate to increase effectiveness.

Extracts from the constituents of pomegranate, i.e., seeds or the inner or outer peel, may also be used alone or in combination with juice. For example, the seeds or the inner or outer peel of pomegranate may be diluted in water and the extract may be made by crushing, squeezing, or extensive vortexing. The insoluble materials of the extract may be separated from the soluble supernatant of the extract. Preferably, the supernatant of the extract is used for the purpose of the present invention, although any oily, lipidic fraction of the extract may also be used. The extract from constituents of pomegranate may be concentrated or diluted, or mixed with each other or with pomegranate juice extract.

In accordance with one embodiment of the present invention, the extract of the present invention may be prepared by a process including the steps of: (a) crushing and squeezing the whole fruits of the pomegranate, including the inner and outer peels and the seeds, to yield a juice component and an insoluble by-product component, and (b) separating the juice component from the insoluble by-product component. The juice component may be used as a juice extract of the present invention. The insoluble by-product component may be resuspended in an aqueous medium, such as, but not limited to, water or alcohol, and be further crushed, squeezed, and mixed to yield a soluble portion and an insoluble portion. Then the soluble portion may be separated from the insoluble portion to produce the extract of the constituents of the present invention. Alternatively, the soluble portion may be combined with the juice extract to produce the extract of the present invention.

In one embodiment of the present invention, the whole fruit of the pomegranate may be enzymatically treated to improve extraction and filtration. For example, pectinase may be used to treat the whole fruit to prevent the formation of pectin gels. Other enzymes known in the art may also be used as long as they can improve extraction and filtration of the extract of the present invention.

The extract of pomegranate of the present invention may be in a liquid or solid form. In accordance with one embodiment of the present invention, a solid form of the extract may be made by lyophilizing the liquid extract of the present invention. Alternatively, the constituents of the pomegranate, such as seeds, inner or outer peels, or any insoluble portion discussed above, may be processed directly to form the solid form of the extract of the present invention. For example, the constituents of the pomegranate may be dried, and "processed into powder or pill forms to be used directly as the solid form of the extract of the present invention.

In one embodiment of the invention pomegranate extract is prepared using the following method. Any one or a combination of the pericarp, inner membrane and seeds are selected and a mixture is formed comprising the pomegranate solids and an aqueous solution. The mixture is then heated to about 60° F. to 210° F., preferably of about 85° F. to 185° F. and optimally of about 110° F. to 160° F. Enzymes are added to the mixture in an amount sufficient to at least partially degrade the pomegranate solids and liberate phytochemicals from the plant tissues and/or cells. Once liberated, the phytochemicals may react and/or polymerize to create new phytochemical compounds or reaction products. The residual insoluble solid materials are removed from the mixture to provide an extract containing phytochemicals. In another embodiment, extracts containing phytochemicals from a pomegranate are provided and used for purposes of the treatment described herein. Such extracts are characterized by a significantly higher total polyphenol content, particularly of the high molecular weight polyphenol (e.g., punicalagin), than is found in pomegranate juice alone. Such extracts may be obtained from the methods disclosed herein.

In a further embodiment of the invention, food products and beverages are provided comprising the extract containing phytochemicals from a pomegranate. In yet a further preferred embodiment, compositions comprising the extract containing phytochemicals from a pomegranate are provided. Such compositions may be in form of tablets, suspensions, implants, solutions, emulsions, capsules, powders, syrups, liquid compositions, ointments, lotions, creams, pastes, and gels. Such compositions may also be in form of pharmaceutical preparations, nutritional supplements, vitamin supplements, food additives, and food supplements.

In a further embodiment of the invention, compositions containing the extract and the pomegranate juice are provided. The combination of the extract and pomegranate juice not only produces a composition having a higher total polyphenol content, as compared to the pomegranate juice alone, but it also provides the broad spectrum of the different polyphenols which predominate the pomegranate juice and extract. In another preferred embodiment, methods are provided for preventing or ameliorating disease conditions in a subject by administering to the subject an effective amount of the composition suitable for use as a pharmaceutical or nutritional preparation. Such disease conditions include polyphenol-mediated diseases and cancer.

In yet another embodiment, methods are provided for modulating the growth and progression of cancerous cells, the methods comprising selecting a subject having cancerous cell growth and administering to the subject an effective amount of the composition containing the extract. In yet a further embodiment, methods are provided for preventing or slowing increases in the Prostate Specific Antigen (PSA) levels in a subject having prostate cancer. The method comprises selecting a subject having prostate cancer and administering to the subject an effective amount of the composition containing the extract.

Compositions used in the various embodiments of the invention described herein may be a variety of kinds, including, but not limited to, nutritional supplements, pharmaceutical preparations, vitamin supplements, food additives, or foods supplements. Compositions of the present invention may be in convenient dosage forms, including, but not limited to, tablets, suspensions, implants, solutions, emulsions, capsules, powders, syrups, liquid compositions, ointments, lotions, creams, pastes, gels, or the like.

Compositions of the present invention may include a carrier. Depending on the kind of compositions of the present invention, a carrier may be a dietary suitable carrier or a pharmaceutically acceptable carrier, as long as it is compatible with the particular kind of compositions of the present invention. Examples of a dietary suitable carrier include, but are not limited to, dietary suitable excipients, diluents, and carriers. Examples of a pharmaceutically acceptable carrier include, but are not limited to, biocompatible vehicles, adjuvants, additives, and diluents to achieve a composition usable as a dosage form. As used herein, the terms "pharmaceutically acceptable," "physiologically tolerable," and grammatical variations thereof, as they refer to compositions, carriers, diluents, and reagents, are used interchangeably and represent that the materials are capable of administration to or upon a mammal without the production of undesirable physiological effects.

The compositions of the present invention may be used alone or in combination with other biologically active ingredients. A composition of the present invention, alone or in combination with other active ingredients, may be administered to a subject in a single dose or multiple doses over a period of time, generally by oral administration. Various administration patterns will be apparent to those skilled in the art. The dosage ranges for the administration of the compositions of the present invention are those large enough to produce the desired effect. The dosage should not be so large as to cause any adverse side effects, such as unwanted cross-reactions and the like. Generally, the dosage will vary with the age, weight, sex, condition, and extent of a condition in a subject, and the intended purpose. The dosage can be adjusted in the event of any counter indications, tolerance, or similar conditions. Those of skill in the art can readily evaluate such factors and, based on this information, determine the particular effective concentration of a composition of the present invention to be used for an intended purpose.

In one embodiment of the present invention, a composition contains the extract of pomegranate in a dosage unit in an amount that contains at least 30 to 3000 µmols per dosage unit of polyphenols. For the purpose of the present invention, polyphenols are those naturally present in the extract of pomegranate. It should be appreciated that polyphenols are used herein as a measurement marker for the amount of extract that needs to be used in each dosage unit. They are not used herein as an indication that they are the active, or the only active, ingredients of the extract. In fact, it is possible that something else, or the synergy of polyphenols and other components of an extract of the present invention, may be responsible for the activities of the extract.

The term "dosage unit" as used herein refers to physically discrete units suitable as unitary dosages for animals, each unit containing a predetermined quantity of active material calculated to produce the desired therapeutic effect in association with the required diluent, e.g., a carrier or vehicle. The specifications for the unit dose of this invention are dictated by and are directly dependent on (a) the unique characteristics of the active material and (b) the limitations inherent in the art of compounding such active material for therapeutical use in animals.

The term "therapeutically effective amount" as used herein means that the amount of the extract of the present invention contained in the composition administered is of sufficient quantity to achieve the intended purpose, such as, in this case, to treat prostate cancer in the patient. For the purpose of the present invention, treatment of prostate cancer may be measured by the increase in the serum prostate specific antigen doubling time (PSADT). For example, digital rectal exam, cystoscopy, transrectal ultrasonography, or prostate biopsy methods may be used to measure stages or grades of prostate cancer.

Accordingly, by determining the increase of prostate specific antigen doubling time in a patient, one can readily determine whether the amount of the extract of the present invention is therapeutically effective. In one embodiment, the therapeutically effective amount of the extract of the present invention contains at least 30 to 3000 μmols of polyphenols naturally occurring in a pomegranate fruit. Again, it should be appreciated that the polyphenols are used herein as a measurement marker for the concentration of the extract of the present invention. In another embodiment, the composition contains one glass of juice extract of the present invention.

The method of the present invention may be used to treat patients with prostate cancer, including patients after prostatectomy, radiotherapy, cryosurgery, or hormonal therapy. In addition, the methods of the present invention may be used to treat in vitro human prostate cancer cell lines, particularly to treat LNCaP, PC-3, CWR22Rvl, or DU145 cells by promoting apoptosis and/or inhibiting proliferation. Furthermore, since tumorigenicity is closely associated with the incidence of prostate cancer, the methods of the present invention may also be used to arrest metastatic spread from the tumor.

Accordingly, another aspect of the present invention provides a method of treating prostate cancer cell lines with serum derived from patients on pomegranate juice treatment. The method comprises the step of administering to the patient a composition comprising an amount of an extract from pomegranate which is therapeutically effective to increase apoptosis and/or decrease cell proliferation of cancer cells. The term "therapeutically effective" as used herein means that the amount of the extract of the present invention contained in the composition administered is of sufficient quantity present in serum to affect apoptosis and proliferation of cancer cells.

The following examples are intended to illustrate, but not to limit, the scope of the invention. Indeed, those of ordinary skill in the art can readily envision and produce further embodiments, based on the teachings herein, without undue experimentation.

EXAMPLES

Methods

Preparation of Pomegranate Juice

Pomegranates (*Punica granatum*, wonderful variety) were picked by hand, washed, chilled to 32° F., and stored in tanks. Then the fruit was crushed, squeezed, and enzymatically treated with pectinase to yield the pomegranate juice and the by-products, which include the inner and outer peels and the seeds. Pectinase hydrolyzes alpha-1,4 galacturonidase bonds in pectin and, thus, it improves extraction and filtration, and prevents the formation of pectin gels. The juice was filtered, pasteurized, concentrated, and stored at −18° C.

For this purpose, the pomegranate juice was lyophilized to remove the aqueous part to yield pomegranate juice concentrate. Each day during the study period, the pomegranate juice concentrate is diluted 1:5 (v:v) with water in order to obtain a single strength pomegranate juice. Total polyphenols concentration in pomegranate juice was determined spectrophotometrically with the phosphomolybdic phosphotungstic acid reagents. It is also possible to use other methods of juice preparation that include extract with higher levels of polyphenols.

Design of the Study and Clinical Endpoints

The 2 year, single center, phase II clinical trial was performed to determine the clinical effect of pomegranate juice on subjects with prostate cancer. The study was fully accrued to 48 subjects in Simon two-stage after efficacy criteria were met based on a 20% response rate, an alpha of 5%, and 90% power. Clinical endpoints included safety, effect on serum PSA, and exploratory laboratory studies. Patients were treated with 8 ounces of pomegranate juice by mouth daily, equivalent to 1.5 mmol of total polyphenols per day.

Human Studies

Eligible subjects had prior prostatectomy or radiotherapy for primary adenocarcinoma, rising serum PSA greater than 0.2 ng/ml and less than 5 ng/ml, and histological confirmed prostate biopsy showing a Gleason score of 7 or less. Just prior to and during the pomegranate juice treatment, the subjects were followed in 3 month intervals for serum PSA, and blood and urine were collected for laboratory studies. Fasting blood samples were obtained from the subjects in the morning, allowed to clot, and then were centrifuged to obtain serum. The serum was frozen and stored at −80° C. until used for analyses. Prior to the pomegranate juice treatment, rising serum PSA levels of the subjects were documented by serial PSA measurement of serum samples of at least one week between each serum sample collection. Safety and tolerability were monitored via continuous adverse event reporting.

Cell Culture

Androgen-dependent LNCaP prostate adenocarcinoma were obtained from American Type Culture Collection (ATCC, Manassas, Va.). The cells were grown in 75-cm2 flasks (Falcon Primaria, Bedford, Mass.) in RPMI-1640 medium without phenol red and supplemented with 10% FBS, 200 IU penicillin, 200 mg/ml streptomycin, and 4 nM L-glutamine (Omega Scientific, Tarzana, Calif.). The cultures were maintained at 37° C. and supplemented with 5% CO2 in a humidified incubator. Cells were passaged routinely at 80% confluence, and fresh medium was replaced every third day. All cells used in the study were from the $10^{th}$ to the $30^{th}$ passage.

Prostate-specific Antigen Assays

Serial measurements of serum samples were analyzed for PSA by using the Immulite third generation PSA assay by Diagnostic Products Corporation, Los Angeles, Calif. Three times or more serial serum PSA levels were measured at an interval of 3 month. The overall PSADT was estimated based on the slope of the linear regression analysis that best fit all available PSA values and computed the doubling time as log 2 divided by the slope.

Analysis of Apoptosis

Induction of apoptosis of LNCaP cells were measured by staining cells with FITC-labeled annexin V. These cells were cultured either with or without serums from patients pretreatment and posttreatment. After 96 hours incubation, cells were harvested and externalized phosphatidylserine at the outer leaflet of the plasma membrane was detected using annexin V-apoptosis detection kit according to the manufacture's instruction (Pharmingen, Inc., San Diego, Calif.).

Proliferation Assay

Cells in the Falcon flasks were detached with 0.25% Trypsin-EDTA solution (Sigma Chemical), centrifuged at 3,000 g for 5 min at 10° C., and resuspended in fresh medium. Cell viability was assessed via Trypan blue exclusion. Cell growth assays were initiated by seeding cells into 96-well plates (Falcon, 53 3072) at various densities in 150 µL culture medium/well (LNCaP 1000 cells/well, PC-3 2000 cells/well). The cells were then incubated for 24 hours at 37° C. to allow attachment. After attachment, medium and non-attached cells were aspirated and replaced with 100 µL fresh culture medium with the same supplementation of antibiotics as indicated before. Growth of cultures was continued for another 24 hours. Then, 50 µL of pre and post treatment serum were added and culture growth continued for 96 hours. Control cells received RMPI-1640 medium only. Cell growth was determined by CellTiter 96AQ assay (Promega, Madison, Wis.).

Urine Sample Analysis

Forty milliliters of urine sample, pomegranate juice pretreatment and posttreatment, was filtered through a Sep-Pak solid phase extraction cartridge (a reverse phase C-18 cartridge; Waters Millipore, United States). The cartridges were previously activated with 10 mL of MeOH and 10 mL of water. Then, the cartridge was washed with 10 mL of water, and the polyphenols fraction was eluted from the cartridge with 2 mL of MeOH. A sample of 100 µL of the methanolic fraction was analyzed by liquid chromatography-tandem mass spectrometry.

The high-performance liquid chromatography (HPLC) system equipped with both a photodiode array detector and a mass detector in series consisted of a HPLC binary pump, autosampler, and degasser controlled by software from Agilent Technologies (Waldbronn, Germany). The mass detector was an ion-trap mass spectrometer (Agilent) equipped with an electrospray ionization (ESI) system (capillary voltage, 4 kV; dry temperature, 350° C.) for the analysis of pomegranate polyphenols in urine samples. The mass detector was equipped with an atmospheric pressure chemical ionization (APCI) system (capillary voltage, 4 kV; dry temperature, 350° C.; crown voltage, 4 kA; APCI temperature, 375° C.).

Statistics

The ANOVA test was performed for all statistical analyses. Results are given as the mean±SEM. Assays in each sample were performed in triplicate. All comparisons are shown for data after pomegranate juice treatment vs. the results obtained before treatment.

Results

There were no serious adverse events reported, and no subjects withdrew because of adverse events. The subjects reported that the pomegranate juice treatment was well tolerated.

Mean PSA doubling time significantly increased with treatment, from a mean of 14 to 26 months (p<0.048). The slope of the mean log PSA decreased from 0.08 to 0.04 on treatment (p<0.019). The result of changes in PSADT pre and post treatment of a subject is summarized in FIG. 1. About 31% of patients achieved a decreased PSA level, with drops ranging from 5% to 85%. About 82.5% of patient achieved a lengthened PSA doubling time.

Figure 2:
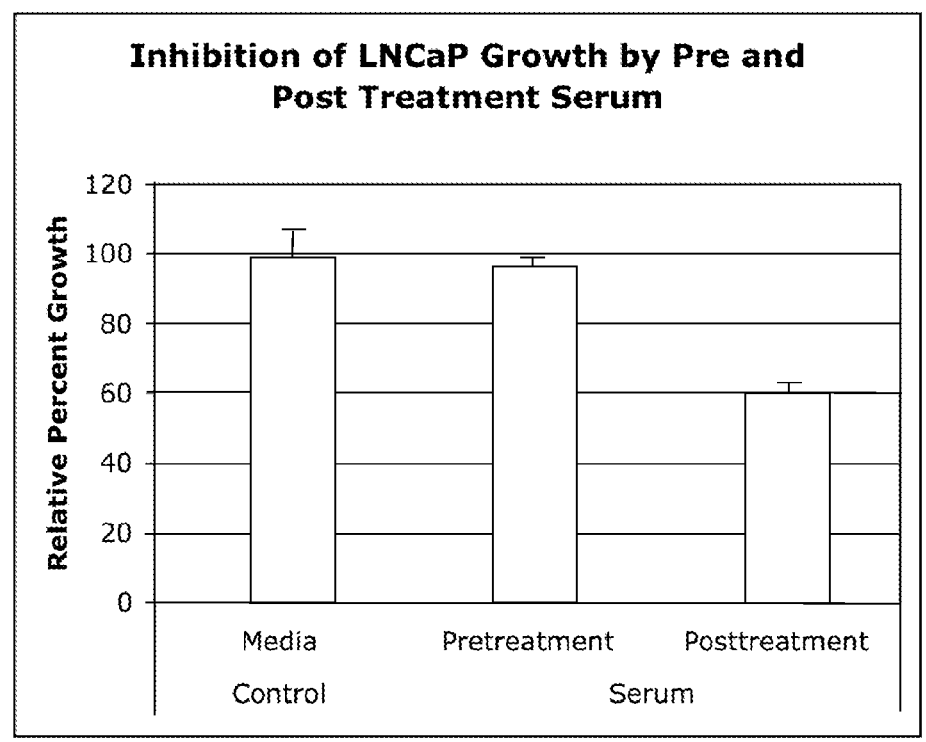
FIG. 2 shows the effect of pre and post treatment serum on growth inhibition of LNCaP cells after 96 hours.

In vitro assays on the growth of LNCaP showed decreased cell proliferation and increased apoptosis (p<0.07) for post treatment patient serum. FIG. 2 shows the effect of pre and post treatment serum on growth inhibition of LNCaP cells. Table 1 shows the effect pre and post treatment serum on apoptosis of LNCaP cells.

Figure 3:
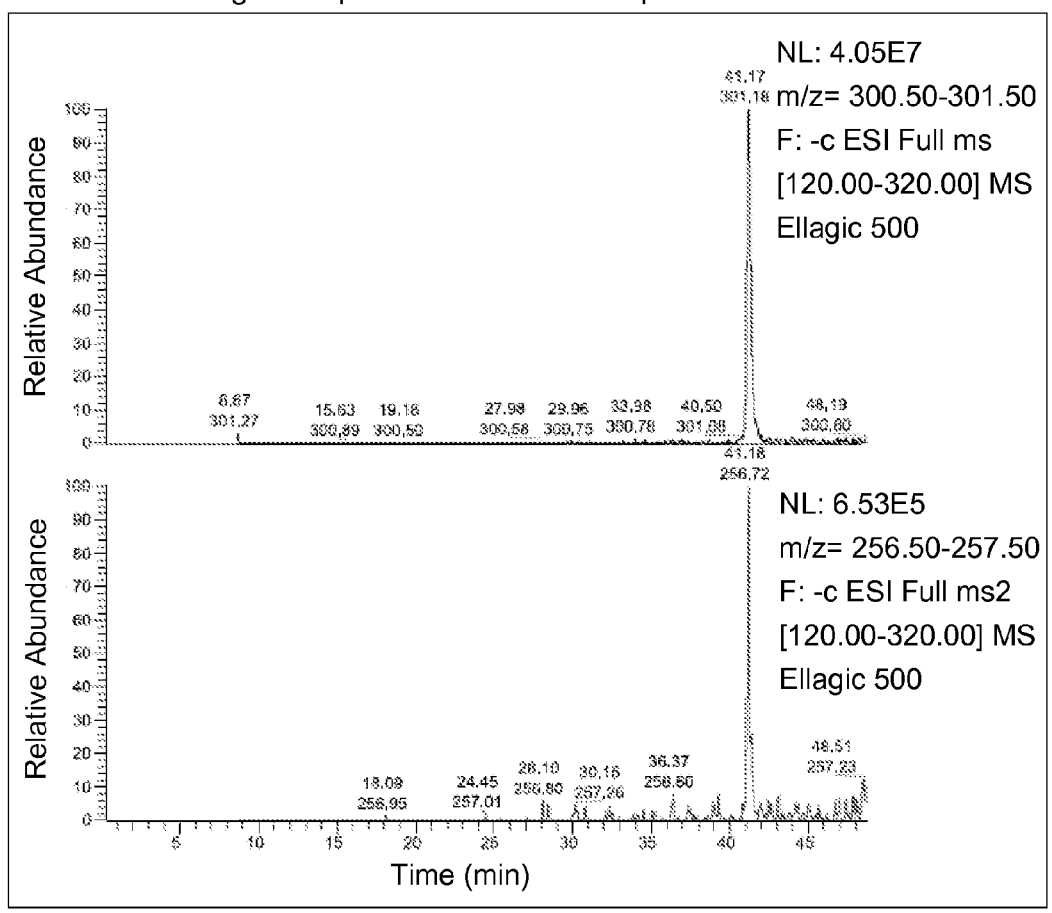
FIG. 3 shows LC-MS analysis of urines, pre and post treatment, obtained from a patient orally administered with pomegranate juice. The relative intensities are given by the figures in the top right hand corner of each chromatogram.

Pomegranate polyphenols were detected of all participants by LC-MS. FIG. 3 shows LC-MS analysis of urines, pre and post treatment, obtained from a patient orally administered with pomegranate juice. The relative intensities are given by the figures in the top right hand corner of each chromatogram.

No patients developed metastatic disease on study.

Discussion

Preclinical and animal data suggest that the pomegranate juice can modulate the growth and progression of prostate cancer. In the pomegranate juice study, the positive and significant beneficial effects on prostate specific antigen (PSA) parameters achieved, coupled with corresponding laboratory effects of post treatment patient serum on prostate cancer in vitro cell growth and apoptosis. The study detected pomegranate polyphenols in urine, which suggest that pomegranate juice is readily absorbed by the body and processed through kidneys.

Laboratory tests showed that serum of patients in vitro reduced cancer cell proliferation and increased cancer cell apoptosis as well. Although it did not reach statistical significance, in vitro assays using pre and post treatment patient serum on the growth of lymph node prostate cancer cell line (LNCaP) also showed decreased cell proliferation and increased apoptosis (P<0.07). This is a highly encouraging result for a substance with no toxicity as this may indicate pomegranate juice dosage be safely escalated. Albrecht et al. study observed that pomegranate juice fractions acutely inhibited in vitro proliferation of LNCaP. PC-3, and DU145 human cancer cell lines . It should be noted that dosages used in Albrecht et al. study for the pomegranate fractions may be higher than used in the pomegranate juice study.

The study was seeking a signal of efficacy for the intervention, and these results activated that signal:

About 71% of the patients had stable disease.
About 31% of patients achieved a decreased PSA level.
About 82.5% of patient achieved a lengthened PSA doubling time.

Doubling time prior to starting therapy averaged about 14 months. After treatment with pomegranate juice the doubling time averaged 26 months, an indication that disease progression had slowed. The change in doubling time was significant at the p=0.0001 level. The slowdown in doubling indicates that the threshold for reaching a level at which metastases could be expected might be extended for several years—possibly not occurring before the patients died of other causes.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A method for increasing a prostate specific antigen (PSA) doubling time in a patient with prostate cancer comprising:
selecting a patient with rising serum PSA; and
administering a daily dosage of a pomegranate extract to said patient with rising serum PSA, wherein said daily dosage comprises about 30 µmols to about 3000 µmols of polyphenols, wherein said pomegranate extract is produced by a process comprising:
crushing and squeezing pomegranate solids suspended in an aqueous solution;
heating said aqueous solution to between about 60° F. to about 210° F.;
adding at least one enzyme to said aqueous solution; and processing said aqueous solution to separate a supernatant from residual insoluble solid materials, wherein said pomegranate extract comprises said supernatant.

2. The method of claim 1, wherein said aqueous solution is heated to between about 85° F. to about 185° F.

3. The method of claim 1, wherein said aqueous solution is heated to between about 100° F. to about 160° F.

4. The method of claim 1, wherein said pomegranate extract is administered daily over an extended period to modulate serum PSA levels.

5. The method of claim 4, wherein said daily dosage comprises about 30 μmol to 3000 μmol of polyphenols.

6. The method of claim 4, wherein said extended period is at least three months.

7. The method of claim 4, wherein said extended period is at least one year.

8. The method of claim 4, wherein said extended period is at least two years.

9. The method of claim 4, wherein said pomegranate extract further comprises a pharmaceutically acceptable carrier.

10. The method of claim 4, wherein said daily dosage is in a form selected from tablets, suspensions, implants, solutions, emulsions, capsules, powders, syrups, liquid compositions, ointments, lotions, creams, pastes, and gels.

11. The method of claim 1, wherein said pomegranate extract is in a form selected from nutritional supplements, pharmaceutical preparations, vitamin supplements, food additives, or foods supplements.

12. The method of claim 1, wherein said pomegranate extract comprises a solid extract.

13. The method of claim 1, wherein said pomegranate extract comprises a liquid extract.

14. A method for modulating the growth and progression of cancerous cells comprising:
   selecting a patient cancerous cell growth; and
   administering a daily dosage of a pomegranate extract, wherein said daily dosage comprises about 30 μmols to about 3000 μmols of polyphenols, wherein said pomegranate extract is formed by:
   crushing and squeezing pomegranate solids suspended in an aqueous solution;
   heating said aqueous solution to between about 60° F. to about 210° F.;
   adding at least one enzyme to said aqueous solution; and
   processing said aqueous solution to separate a supernatant from residual insoluble solid materials, wherein said pomegranate extract comprises said supernatant.

15. The method of claim 14, wherein said aqueous solution is heated to between about 85° F. to about 185° F.

16. The method of claim 14, wherein said aqueous solution is heated to between about 100° F. to about 160° F.

17. The method of claim 14, wherein said pomegranate extract is administered daily over an extended period to modulate the growth of cancerous cells.

18. The method of claim 17, wherein said daily dosage is in a form selected from tablets, suspensions, implants, solutions, emulsions, capsules, powders, syrups, liquid compositions, ointments, lotions, creams, pastes, and gels.

* * * * *